(12) United States Patent
Yahata

(10) Patent No.: US 7,203,268 B2
(45) Date of Patent: Apr. 10, 2007

(54) X-RAY CT SYSTEM AND X-RAY APPARATUS

(75) Inventor: Mitsuru Yahata, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/069,850

(22) Filed: Mar. 1, 2005

(65) Prior Publication Data

US 2005/0195935 A1     Sep. 8, 2005

(30) Foreign Application Priority Data

Mar. 2, 2004     (JP)     ............... 2004-057154

(51) Int. Cl.
*A61B 6/00*     (2006.01)
(52) U.S. Cl. ............................. 378/4; 378/15
(58) Field of Classification Search ............... 378/4, 378/15, 124, 901
See application file for complete search history.

(56) References Cited

U.S. PATENT DOCUMENTS

| | | | |
|---|---|---|---|
| 5,825,842 A | 10/1998 | Taguchi | 378/15 |
| 6,201,849 B1 | 3/2001 | Lai | 378/4 |
| 6,256,365 B1 | 7/2001 | Lai | 378/4 |
| 6,256,366 B1 | 7/2001 | Lai | 378/4 |
| 6,285,733 B1 | 9/2001 | Proksa et al. | 378/15 |
| 7,042,975 B2 * | 5/2006 | Heuscher | 378/8 |
| 2003/0108146 A1 * | 6/2003 | Malamud | 378/19 |
| 2005/0147201 A1 * | 7/2005 | Hoffman | 378/15 |

FOREIGN PATENT DOCUMENTS

| | | |
|---|---|---|
| JP | 2003-144429 | 5/2003 |
| JP | 2003-203797 | 7/2003 |

OTHER PUBLICATIONS

An English translation of JP 06-1258888.
A Japanese language communication from the Japanese Patent Office.

* cited by examiner

*Primary Examiner*—Courtney Thomas
(74) *Attorney, Agent, or Firm*—Carl B. Horton, Esq.; Armstrong Teasdale LLP

(57) ABSTRACT

An X-ray CT system comprises: an X-ray generator that generates two cone beam X-radiations which pass through two successive slabs; an X-ray detector that detects a two-dimensional distribution of intensities exhibited by the two cone beam X-radiations having passed through the two slabs; an acquisition unit that acquires a plurality of view of projection data representing the two slabs on the basis of detection signals sent from the X-ray detector; and a reconstruction unit that reconstructs an image according to the projection data.

16 Claims, 5 Drawing Sheets

US 7,203,268 B2

X-RAY CT SYSTEM AND X-RAY APPARATUS

CROSS REFERENCE TO RELATED APPLICATIONS

This application claims the benefit of Japanese Application No. 2004-57154 filed Mar. 2, 2004.

BACKGROUND OF THE INVENTION

The present invention relates to an X-ray computed tomography (CT) system and an X-ray apparatus. More particularly, the present invention is concerned with an X-ray CT system that scans a three-dimensional region with a cone beam X-radiation, and an X-ray apparatus for the X-ray CT system.

In X-ray CT systems, a cone beam X-radiation is used to radiograph a three-dimensional region (slab) in a subject during one scan. A two-dimensional array detector detects a two-dimensional distribution of intensities exhibited by the cone beam X-radiation having passed through the slab (projection). An image is then reconstructed based on a plurality of views of projection data.

A cone beam algorithm is used to reconstruct an image. A typical cone beam algorithm is a Feldkamp algorithm (refer to, for example, Patent Document 1).

[Patent Document 1] Japanese Unexamined Patent Application Publication No. 2003-144429 (p. 4)

When any of cone beam algorithms represented by the Feldkamp algorithm is employed, a slab thickness permissible for radiography during one scan, that is, the size in a body-axis direction of a three-dimensional region is about 80 mm at maximum in practice. If the thickness is equal to or larger than 80 mm, image quality is degraded due to an increase in the number of artifacts in a reconstructed image.

SUMMARY OF THE INVENTION

Therefore, an object of the present invention is to realize an X-ray CT system offering a large slab thickness permissible for radiography during one scan, and an X-ray apparatus for the X-ray CT system.

(1) According to one aspect of the present invention for accomplishing the above object, there is provided an X-ray CT system comprising: an X-ray generating means for generating a plurality of cone beam X-radiations that passes through a plurality of successive slabs; an X-ray detecting means for detecting a two-dimensional distribution of intensities exhibited by cone beam X-radiations having passed through the plurality of slabs; an acquiring means for acquiring a plurality of views of projection data, which represents the plurality of slabs, on the basis of detection signals sent from the X-ray detecting means; and a reconstructing means for reconstructing an image according to the projection data.

(2) According to another aspect of the present invention for accomplishing the aforesaid object, there is provided an X-ray apparatus comprising: an X-ray generating means for generating a plurality of cone beam X-radiations that passes through a plurality of successive slabs; and an X-ray detecting means for detecting a two-dimensional distribution of intensities exhibited by the plurality of cone beam X-radiations having passed through the plurality of slabs.

Preferably, the plurality of cone beam X-radiations asynchronously passes through adjoining slabs from the viewpoint of avoiding overlap of projections of the slabs. Preferably, the X-ray generating means has X-ray generation spots in association with the plurality of slabs from the viewpoint of appropriately generating a plurality of cone beam X-radiations. Preferably, the X-ray generating means includes a collimator in association with the X-ray generation spots, from the viewpoint of appropriately forming a plurality of cone beam X-radiations.

Preferably, the X-ray generating means includes an X-ray tube, which has a plurality of X-ray focal spots in association with the plurality of slabs, from the viewpoint of appropriately generating a plurality of cone beam X-radiations. Preferably, the X-ray tube includes a plurality of pairs of an anode and a cathode in association with the plurality of slabs from the viewpoint of appropriately offering a plurality of focal spots. Preferably, the X-ray tube has a plurality of grids associated with the plurality of pairs of an anode and a cathode from the viewpoint of controlling the timings of generating a plurality of cone beam X-radiations. Preferably, the number of successive slabs is two from the viewpoint of offering an overall slab thickness that is twice as large as the conventional one.

According to the foregoing aspects of the present invention, the present invention includes the X-ray generating means for generating a plurality of cone beam X-radiations that passes through a plurality of successive slabs and the X-ray detecting means for detecting a two-dimensional distribution of intensities exhibited by the plurality of cone beam X-radiations having passed through the plurality of slabs. Therefore, while the thickness of each of the slabs is set to a value permitting image reconstruction based on a cone beam algorithm, the overall slab thickness, that is, the overall thickness of the plurality of slabs can be increased.

Further objects and advantages of the present invention will be apparent from the following description of the preferred embodiments of the invention as illustrated in the accompanying drawings.

DETAILED DESCRIPTION OF THE INVENTION

Figure 1:
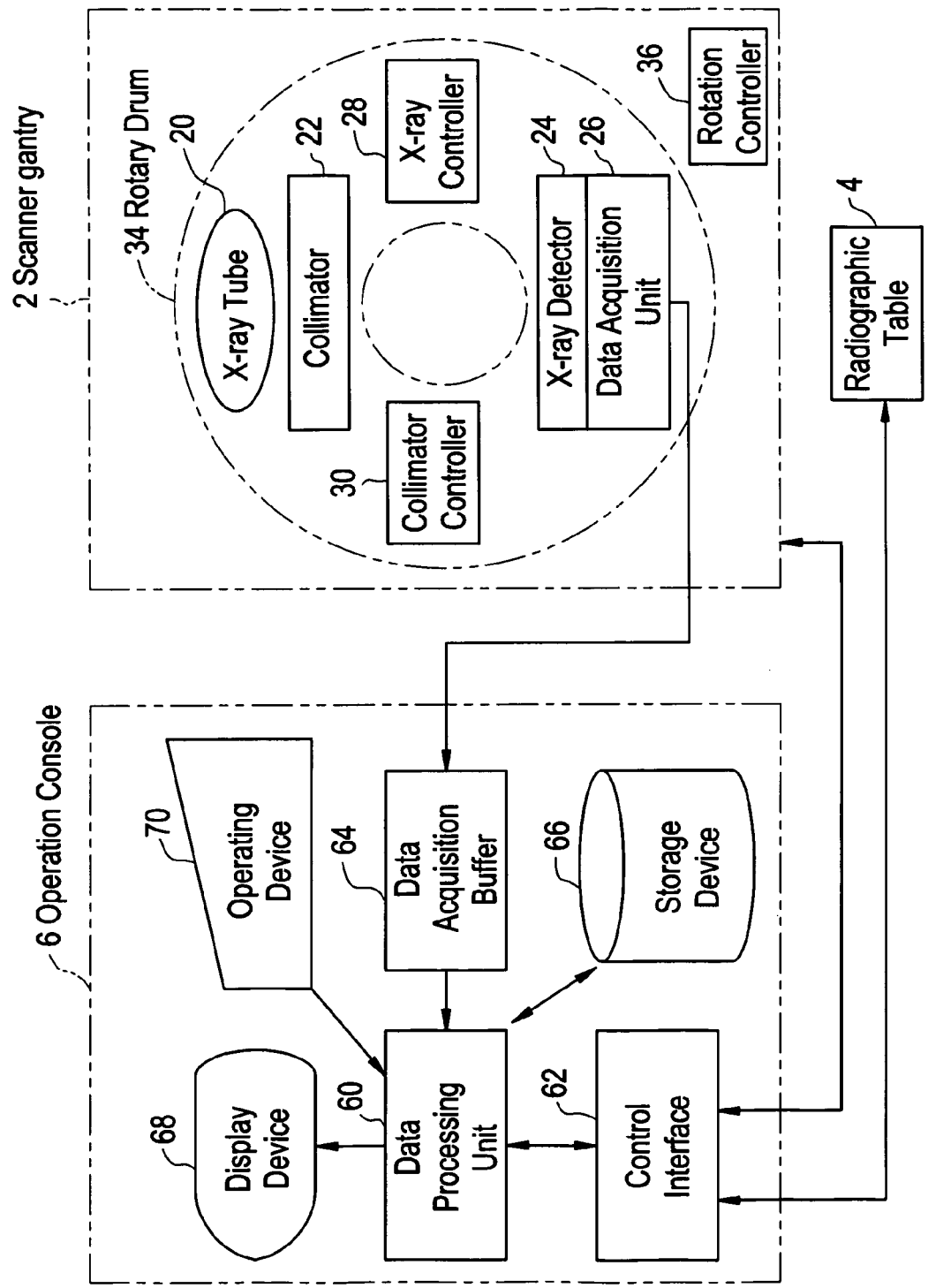
FIG. 1 is a block diagram of an X-ray CT system that is the best mode for implementing the present invention.

Referring to drawings, the best mode for implementing the present invention will be described below. Noted is that the present invention is not limited to the best mode for implementing the present invention. FIG. 1 is a block diagram of an X-ray CT system. The X-ray CT system is an example of the best mode for implementing the present invention. The configuration of the X-ray CT system provides an example of the best mode for implementing the present invention in an X-ray CT system. Moreover, part of the configuration of the X-ray CT system provides an example of the best mode for implementing the present invention in an X-ray apparatus.

As shown in FIG. 1, the X-ray CT system comprises a scanner gantry 2, a radiographic table 4, and an operator console 6. The scanner gantry 2 includes an X-ray tube 20. X-rays radiated from the X-ray tube 20 and not shown are recomposed or collimated into a conical X-ray beam or a cone beam X-radiation by a collimator 22, and then irradiated to an X-ray detector 24. The assembly of the X-ray tube 20 and collimator 22 is an example of an X-ray generating means included in the present invention. The X-ray tube 20 is an example of an X-ray tube included in the present invention. The collimator 22 is an example of a collimator included in the present invention.

The X-ray detector 24 includes a plurality of detector elements arranged in a two-dimensional array along with the spread of a cone beam X-radiation. The X-ray detector 24 is an example of an X-ray detecting means included in the present invention. The configuration of the X-ray detector 24 will be described later. A subject of radiography is carried into a space between the X-ray tube 20 and X-ray detector 24 while lying down on the radiographic table 4.

As described later, the X-ray tube 20 has a plurality of focal spots and generates X-ray beams from the focal spots. The collimator 22 collimates the plurality of X-radiations. The X-ray tube 20, collimator 22, and X-ray detector 24 constitute X-irradiation/detection equipment. The X-irradiation/detection equipment will be described later.

A data acquisition unit 26 is connected to the X-ray detector 24. The data acquisition unit 26 acquires detection signals, which are sent from the respective detector elements included in the X-ray detector 24, in the form of digital data. The X-ray detector 24 and data acquisition unit 26 constitute an example of an acquiring means included in the present invention. The detection signals sent from the detector elements serve as a signal representing a projection of a subject produced with X-rays. The signal shall be called projection data or merely data.

X-irradiation from the X-ray tube 20 is controlled by an X-ray controller 28. The illustration of the connective relationship between the X-ray tube 20 and X-ray controller 28 will be omitted. The collimator 22 is controlled by a collimator controller 30. The illustration of the connective relationship between the collimator 22 and collimator controller 30 will be omitted.

The foregoing components starting with the X-ray tube 20 and ending with the collimator controller 30 are incorporated in a rotary drum 34 included in the scanner gantry 2, and can be rotated about a subject of radiography. The rotation of the rotary drum 34 is controlled by a rotation controller 36. The illustration of the connective relationship between the rotary drum 34 and rotation controller 36 will be omitted.

The operator console 6 includes a data processing unit 60. The data processing unit 60 is realized with, for example, a computer. A control interface 62 is connected to the data processing unit 60. The scanner gantry 2 and radiographic table 4 are connected to the control interface 62. The data processing unit 60 controls the scanner gantry 2 and radiographic table 4 via the control interface 62.

The data acquisition unit 26, X-ray controller 28, collimator controller 30, and rotation controller 36 incorporated in the scanner gantry 2 are controlled via the control interface 62, whereby a subject of radiography is scanned. The illustration of the connections of these components to the control interface 62 will be omitted.

A data acquisition buffer 64 is connected to the data processing unit 60. The data acquisition unit 26 incorporated in the scanner gantry 2 is connected to the data acquisition buffer 64. Data acquired by the data acquisition unit 26 is transferred to the data processing unit 60 via the data acquisition buffer 64.

A storage device 66 is connected to the data processing unit 60. Projection data transferred to the data processing unit 60 via the data acquisition buffer 64 and control interface 62 is stored in the storage device 66. Moreover, programs for giving instructions to the data processing unit 60 are stored in the storage device 66. The data processing unit 60 runs any of the programs, whereby an action is performed in the X-ray CT system.

The data processing unit 60 reconstructs an image using a plurality of views of projection data that is stored in the storage device 66 via the data acquisition buffer 64. The data processing unit 60 is an example of a reconstructing means included in the present invention. For image reconstruction, a cone beam algorithm, for example, a Feldkamp algorithm is employed.

A display device 68 and an operating device 70 are connected to the data processing unit 60. The display device 68 is realized with a graphic display or the like. The operating device 70 is realized with a keyboard having a pointing device.

A reconstructed image sent from the data processing unit 60 and other information are displayed on the display device 68. A user manipulates the operating unit 70 so as to enter various instructions or pieces of information that are transmitted to the data processing unit 60. The user uses the display device 68 and operating device 70 to interactively operate the X-ray CT system.

Figure 2:
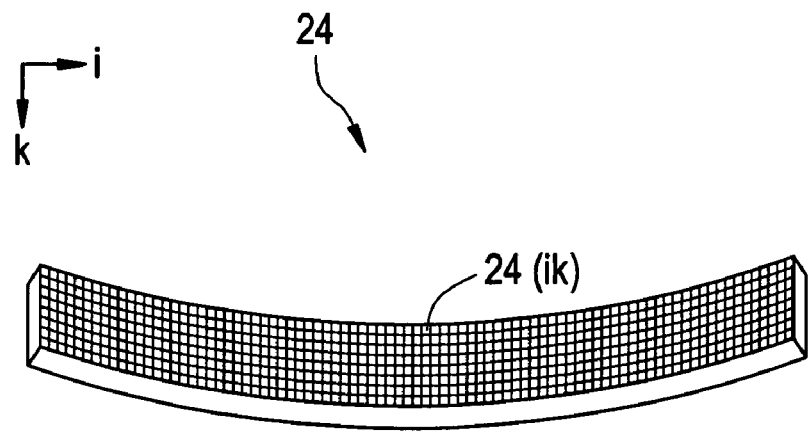
FIG. 2 shows the configuration of an X-ray detector.

FIG. 2 illustratively shows the configuration of the X-ray detector 24. As illustrated, the X-ray detector 24 is a multi-channel X-ray detector having a plurality of X-ray detector elements 24(ik) arranged in a two-dimensional array. The plurality of X-ray detector elements 24(ik) forms a cylindrically concave X-ray receiving surface as a whole.

Herein, i denotes a channel number that is, for example, 1, 2, . . . , 1000, and k denotes a row number that is, for example, 1, 2, . . . , 240. The X-ray detector elements 24(ik) having the same row number k constitute a detector element array. The number of detector element arrays constituting the X-ray detector 24 is not limited to 240 but may be any value.

Each of the X-ray detector elements 24(ik) is realized with, for example, a combination of a scintillator and a photodiode. The present invention is not limited to this combination. Alternatively, a semiconductor X-ray detector element utilizing cadmium telluride or an ionization chamber type X-ray detector element utilizing a xenon gas may be adopted.

Figure 3A:
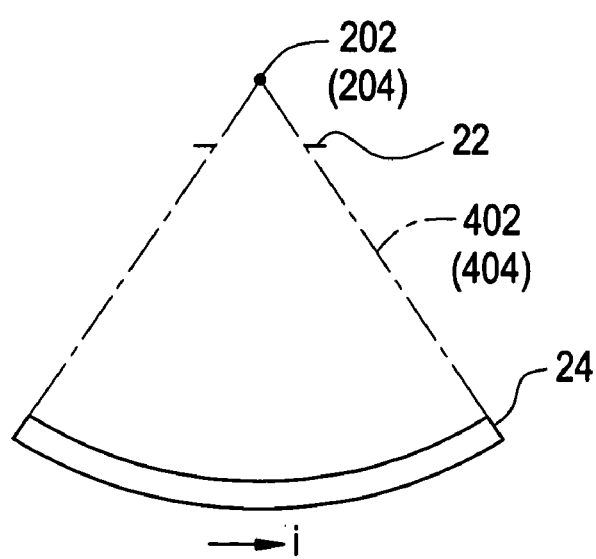
FIGS. 3a and 3b show the configuration of X-irradiation/detection equipment.
Figure 3B:
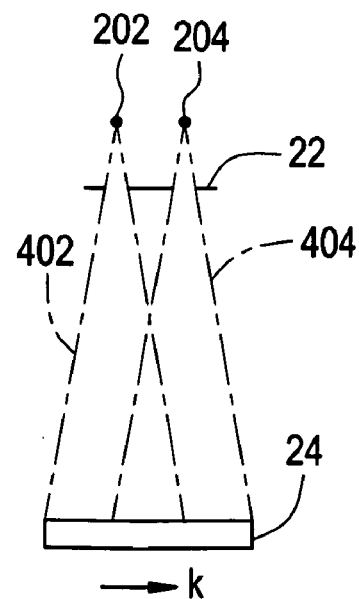

FIG. 3 shows the correlation among the X-ray tube 20, collimator 22, and X-ray detector 24 that are included in the X-irradiation/detection equipment. In the drawing, the X-ray tube 20 is represented by X-ray focal spots. Hereinafter, the X-ray focal spot may be simply called a focal spot. FIG. 3(a) shows the correlation observed in front of the scanner gantry 2, while FIG. 3(b) shows the correlation observed by the side of the scanner gantry 2.

As illustrated, the X-ray tube 20 has two focal spots 202 and 204. X-rays radiated from the focal spots 202 and 204 are recomposed into two cone beam X-radiations 402 and 404 by means of the collimator 22, and then irradiated to the X-ray detector 24.

FIG. 3(a) shows the spreads in one direction of the cone beam X-radiations 402 and 404. Hereinafter, this direction may be called a width direction. The width direction of the cone beam X-radiations 402 and 404 corresponds to the direction in which channels are juxtaposed in the X-ray detector 24. FIG. 3(b) shows the spreads in other direction of the cone beam X-radiations 402 and 404. This direction may be called the thickness direction of the cone beam X-radiations 402 and 404. The thickness direction of the cone beam X-radiations 402 and 404 corresponds to a direction in which the plurality of detector element arrays is juxtaposed in the X-ray detector 24.

Figure 4:
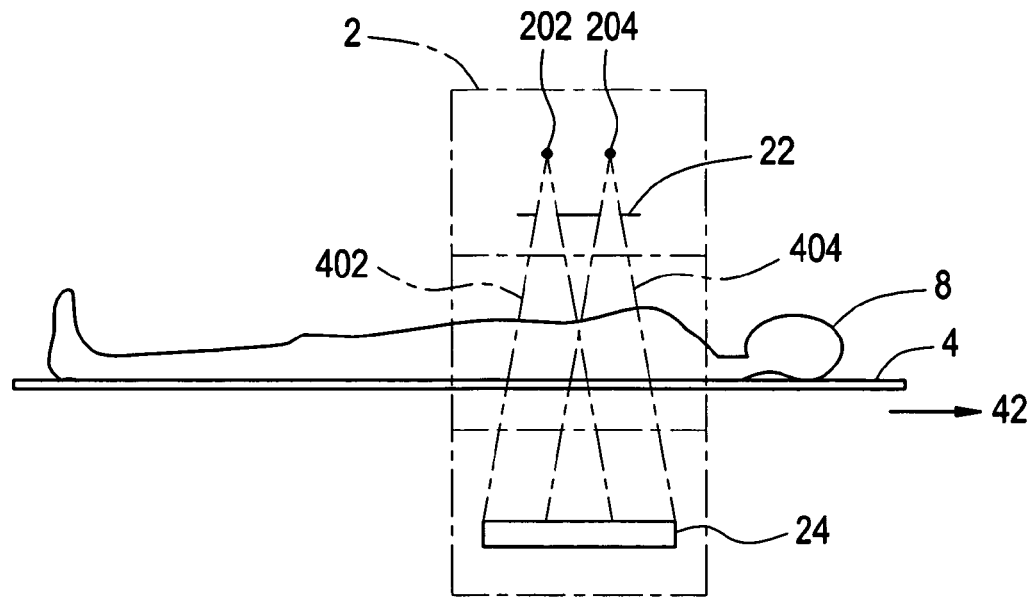
FIG. 4 shows the relationship between the X-irradiation/detection equipment and a subject.

A subject 8 is, for example, as shown in FIG. 4, carried into an X-irradiation space while lying down on the radiographic table 4 with his/her body axis intersecting the cone beam X-radiations 402 and 404. The scanner gantry 2 has a cylindrical structure in which the X-irradiation/detection equipment is incorporated. The X-irradiation space is defined in an internal space of the cylindrical structure of the scanner gantry 2. The cone beam X-radiations 402 and 404 pass through the subject 8 and fall on the X-ray detector 24. The X-ray detector 24 detects a two-dimensional distribution of intensities exhibited by the transmitted X-radiations.

When the X-irradiation/detection equipment is rotated with the radiographic table 4 at a halt, an axial scan is achieved. When the radiographic table 4 is, as indicated with an arrow 42, continuously moved in the direction of the body axis of the subject 8 concurrently with the rotation of the X-irradiation/detection equipment, the X-irradiation/detection equipment follows a helical trajectory, which encloses the subject 8, relatively to the subject. Consequently, a so-called helical scan is achieved.

A plurality (for example, about 1000) of views of projection data is acquired during one scan. The acquisition of projection data is achieved by the system of the X-ray detector 24, data acquisition unit 26, and data acquisition buffer 64.

Figure 5:
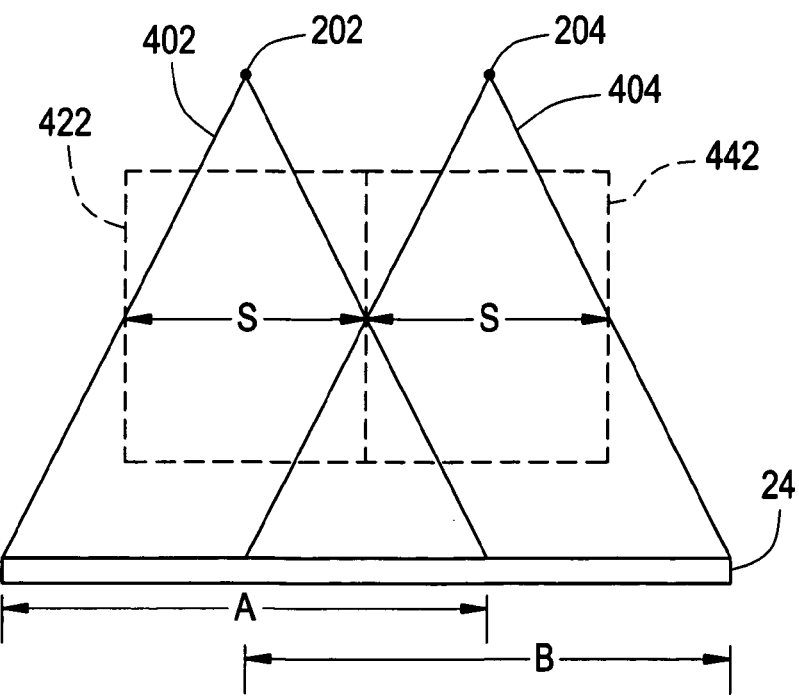
FIG. 5 shows the relationship between two cone beam X-radiations.
Figure 6:
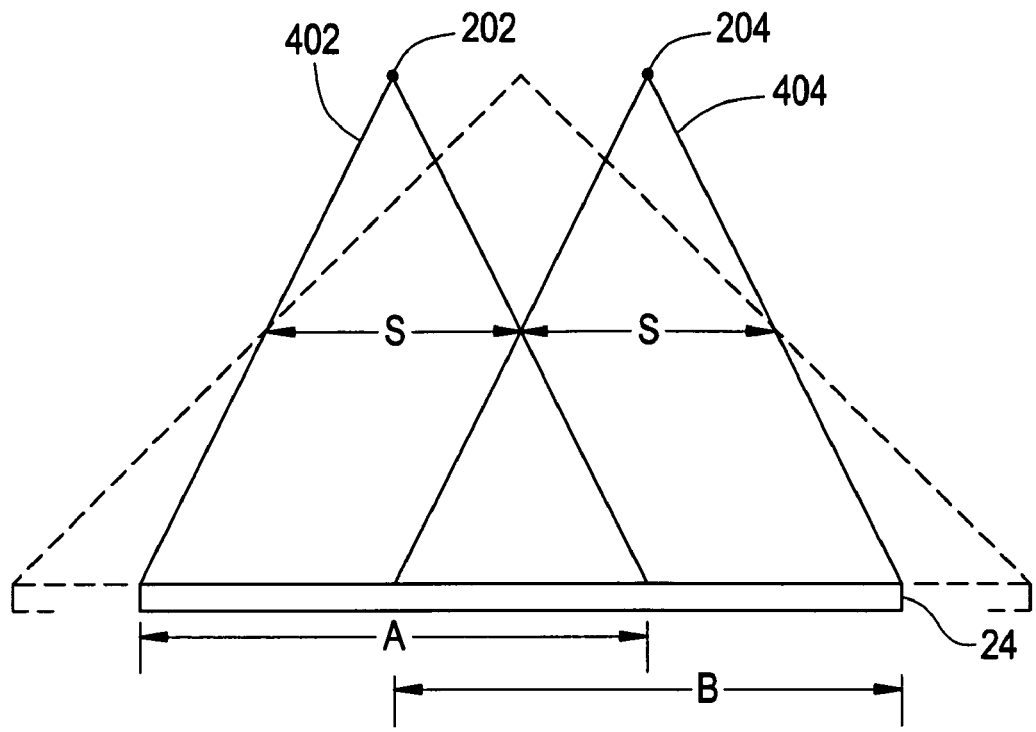
FIG. 6 shows the relationship between two cone beam X-radiations.

The two cone beam X-radiations 402 and 404 will be described below. FIG. 5 illustratively shows the relationship between the two cone beam X-radiations 402 and 404. FIG. 5 has an observer's eye located at the same position as FIG. 3(b) does. As shown in FIG. 6, the two cone beam X-radiations 402 and 404 generated from the two focal spots 202 and 204 pass through successive slabs 422 and 442. The slabs 422 and 442 are two slabs succeeding in the body-axis direction.

The X-ray tube 20 has the two X-ray generation spots (focal spots) in association with two slabs, and can therefore appropriately generate two cone beam X-radiations. Moreover, since the collimator supporting the two X-ray generation spots is included, the two cone beam X-radiations can be appropriately formed.

The thickness of each of the slabs 422 and 442 is set to a maximum value S (for example, 80 mm) permitting image reconstruction to be performed based on a cone beam algorithm without causing an artifact. Consequently, the overall thickness of the two slabs 422 and 442 comes to 2S (for example, 160 mm).

The employment of two cone beam X-radiations passing through two successive slabs realizes a slab thickness that is twice as large as the conventional limit permissible for radiography. The slab thickness is an overall thickness of a slab or slabs on a plane containing an isocenter.

X-rays having passed through the slab 422 are detected by X-ray detector elements belonging to a range A in the X-ray detector 24. Based on detection signals sent from the X-ray detector elements, an image representing the slab 422 is reconstructed according to a cone beam algorithm. X-rays having passed through the slab 442 are detected by X-ray detector elements belonging to a range B in the X-ray detector 24. Based on detection signals sent from the X-ray detection elements, an image representing the slab 442 is reconstructed according to the cone beam algorithm. The thickness of each of the slabs 422 and 442 is set to a value permitting image reconstruction to be performed based on the cone beam algorithm without causing an artifact. Therefore, a good-quality image can be reconstructed.

Other advantage provided by the employment of two cone beam X-radiations 402 and 404 is that an increase in the area of a light receiving surface of the X-ray detector 24 is small for an increase in a slab thickness. Namely, supposing slabs having the same thickness are radiographed with a sole cone beam X-radiation, since the sole cone beam X-radiation spreads, the light receiving surface of the X-ray detector 24 must be larger than it is when two cone beam X-radiations are employed. Therefore, the X-ray detector cannot help being designed to be large in size.

Figure 7:
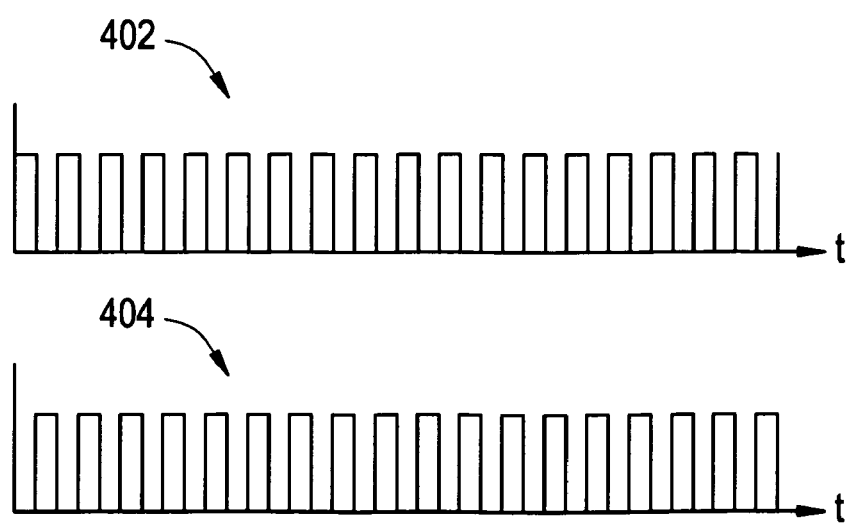
FIG. 7 shows the timings of irradiating two cone beam X-radiations.

The ranges A and B within which the cone beam X-radiations 402 and 404 are received overlap. The cone beam X-radiations 402 and 404 are therefore alternately irradiated as shown in the timing chart of FIG. 7 in order to avoid mixing of detection signals detected by the X-ray detector elements belonging to the overlapping parts of the ranges A and B. When the two cone beam X-radiations asynchronously pass through adjoining slabs, double radiography of parts of slabs can be avoided.

Figure 8:
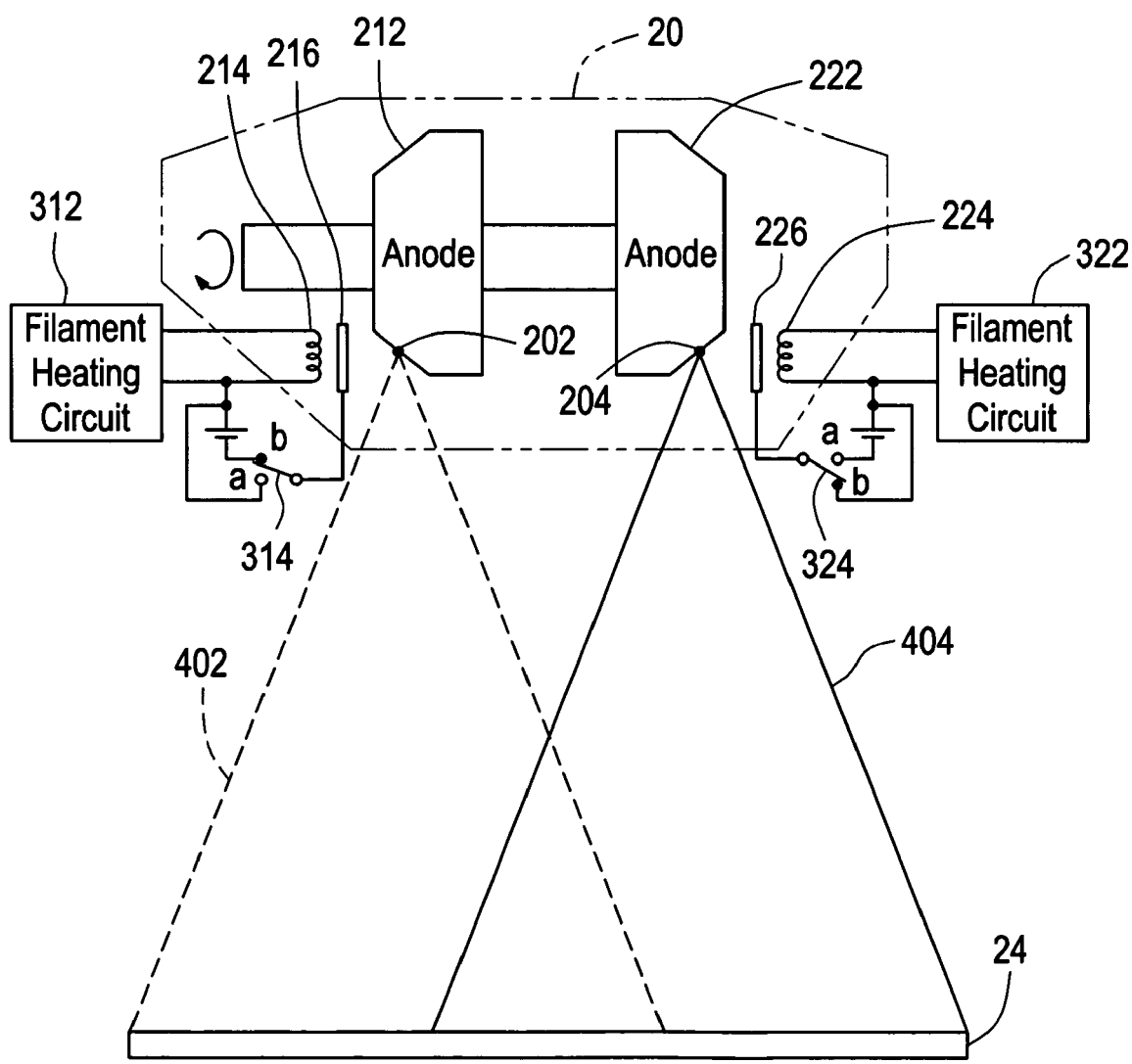
FIG. 8 shows the configuration of an X-ray tube having two focal spots.

FIG. 8 shows an example of a configuration including the X-ray tube 20 and control circuits that permit alternate X-irradiations. As shown in FIG. 8, the X-ray tube 20 comprises a set of an anode 212, a cathode 214, and a grid 216 and a set of an anode 222, a cathode 224, and a grid 226.

A filament current is fed to the cathode 214 or 224 by a filament heating circuit 312 or 322. A bias voltage is applied to the grid 216 or 226 after being set to either of two levels by switch 314 or 324.

The two levels to which the bias voltage is set are 0 V and a negative voltage. The negative voltage assumes a value permitting blocking of an electron flow between a cathode and an anode. Consequently, X-irradiation can be discontinued by changing the connections to be made via the switch 314 or 324. The connections to be made via the switch 314 or 324 are changed with either of signals that are out of phase with each other. Eventually, the cone beam X-radiations 402 and 404 are alternately generated from the focal spots 202 and 204 respectively.

As mentioned above, since an X-ray tube having two X-ray focal spots in association with two slabs is employed, two cone beam X-radiations can be appropriately generated. Since the X-ray tube includes two anodes and two cathodes in association with two slabs, two focal spots can be appropriately offered. Moreover, since the X-ray tube has two grids associated with the two pairs of an anode and a cathode, the timings of generating two cone beam X-radiations can be controlled.

The best mode for implementing the present invention has been described in reference to an example in which the number of successive slabs is two. The number of successive slabs is not limited to two but may be any value equal to or larger than 2.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT system comprising:
   an X-ray generating device for generating a plurality of cone beam X-radiations that passes through different respective ones of a plurality of slabs each having a width in a body-axis direction, each of said slab widths is permissible for radiography during one scan by one cone beam X-radiation, wherein said slabs are joined in the body-axis direction and the plurality of cone beams X-radiations are asynchronously irradiated;
   an X-ray detecting device for detecting a two-dimensional distribution of intensities exhibited by all of the plurality of cone beam X-radiations having passed through the plurality of slabs;
   an acquiring device for acquiring a plurality of views of projection data, which represents the plurality of slabs, on the basis of detection signals sent from said X-ray detecting device; and
   a reconstructing device for reconstructing an image according to the projection data.

2. CT system according to claim 1, wherein said X-ray generating device generates two cone beam X-radiations and one of the two cones beam X-radiations is alternately irradiated compared to another one of the two cone beam X-radiations.

3. An X-ray CT system according to claim 1, wherein said X-ray generating device has X-ray generation spots in association with the plurality of slabs.

4. An X-ray CT system according to claim 3, wherein said X-ray generating device includes a collimator that supports the X-ray generation spots.

5. An X-ray CT system according to claim 1, wherein said X-ray generating device includes an X-ray tube that has a plurality of X-ray focal spots in association with the plurality of slabs.

6. An X-ray CT system according to claim 5, wherein said X-ray tube includes a plurality of pairs of an anode and a cathode in association with the plurality of slabs.

7. An X-ray CT system according to claim 6, wherein said X-ray tube has a plurality of grids associated with said plurality of pairs of an anode and a cathode.

8. An X-ray CT system according to claim 1, wherein the number of successive slabs is two.

9. An X-ray apparatus comprising:
   an X-ray generating device for generating a plurality of cone beam X-radiations that passes through different respective ones of a plurality of slabs each having a width in a body-axis direction, each of said slab widths is permissible for radiography during one scan by one cone beam X-radiation, wherein said slabs are joined in the body-axis direction and the plurality of cone beam X-radiations are asynchronously irradiated; and
   an X-ray detecting device for detecting a two-dimensional distribution of intensities exhibited by all of the plurality of cone beam X-radiations having passed through the plurality of slabs.

10. An X-ray apparatus according to claim 9, wherein one of the plurality of cone beam X-radiations is alternately irradiated compared to another one of the plurality of cone beam X-radiations.

11. An X-ray apparatus according to claim 9, wherein said X-ray generating device has X-ray generation spots in association with the plurality of slabs.

12. An X-ray apparatus according to claim 11, wherein said X-ray generating device includes a collimator that supports the X-ray generation spots.

13. An X-ray apparatus according to claim 9, wherein said X-ray generating device includes an X-ray tube that has a plurality of X-ray focal spots in association with the plurality of slabs.

14. An X-ray apparatus according to claim 13, wherein said X-ray tube includes a plurality of pairs of an anode and a cathode in association with the plurality of slabs.

15. An X-ray apparatus according to claim 14, wherein said X-ray tube has a plurality of grids associated with said plurality of pairs of an anode and a cathode.

16. An X-ray apparatus according to claim 9, wherein the number of successive slabs is two.

* * * * *